United States Patent [19]

Balassa

[11] Patent Number: 4,656,137
[45] Date of Patent: Apr. 7, 1987

[54] METHOD OF PROCESSING ANIMAL CARTILAGE

[75] Inventor: Leslie L. Balassa, Blooming Grove, N.Y.

[73] Assignee: Lescarden Inc, New York, N.Y.

[21] Appl. No.: 775,492

[22] Filed: Sep. 12, 1985

[51] Int. Cl.$^4$ .................. C07G 17/00; A61K 35/32
[52] U.S. Cl. .................................. 435/267; 424/95; 426/417
[58] Field of Search .................. 424/95; 435/267; 426/417; 62/66

[56] References Cited

U.S. PATENT DOCUMENTS

| | | | |
|---|---|---|---|
| 3,071,477 | 1/1963 | Klevens | 426/417 |
| 3,141,774 | 7/1964 | Little | 426/417 |
| 3,586,515 | 6/1971 | Anderson | 426/417 |

*Primary Examiner*—Sam Rosen
*Attorney, Agent, or Firm*—Darby & Darby

[57] ABSTRACT

Disclosed is a method of preparing finely divided cartilage powder from raw cartilage including the steps of mechanically trimming raw cartilage from an animal body, and granulating the raw cartilage into granules having an average size of from about 4 mm to 8 mm diameter. The granules are then subjected to azeotropic extraction, the extraction conducted with an extracting agent which both forms an azeotrope with water and solubilizes fat. The granules are then separated from the extracting agent, and milled to an average size of from about 40 to 70$\mu$ diameter.

Also disclosed is a method of separating calcium compounds from cartilage including the steps of mechanically trimming raw cartilage from an animal body, granulating the raw cartilage into granules having an average size of from about 4 to 8 mm diameter, and partially drying the granules to produce a friable calcified outer layer on each granule. The granules are then subjected to mechanical agitation to pulverize the friable calcified outer layer and separated from the pulverized calcified outer layer.

Also disclosed is a method of preparing finely divided cartilage powder involving a freeze-drying step.

4 Claims, No Drawings

METHOD OF PROCESSING ANIMAL CARTILAGE

This invention pertains to cartilage extraction processes and products. More specifically, the invention relates to a process for preparing a biologically active cartilage product using raw animal or fish cartilage together with adhering tissue as the starting material.

The preparation of powdered cartilage products for various therapeutic applications is discussed in the prior art. Thus, U.S. Pat. Nos. 3,772,432, Re. 28,093, 3,966,908 and 3,476,855 teach the preparation of pharmaceutical materials from raw cartilage.

Cartilage harvested from animal bodies has substantial quantities of adhering proteinaceous and fatty tissues which are largely removed by mechanical trimming. For the preparation of pharmaceuticals the trimmed cartilage has to be further freed of the remaining foreign tissues. This is usually accomplished by digesting the trimmed cartilage in a solution containing a proteolytic enzyme which may be one or a combination of pepsin, papain trypsin or other enzymes in a dilute solution of hydrochloric or acetic acid.

Typically, the enzyme-treated cartilage is washed with water, preferably distilled or deionized water, until no enzyme can be detected in the effluent. The cartilage at this point still contains 3 to 8% of fat and up to about 80% of water of hydration (depending on the cartilage source).

The washed, enzyme-treated cartilage is granulated in a swing hammer mill or other suitable granulating equipment such as a shredder or by passing through the blades of a meat grinder. The purpose of this step is to increase the surface area of the cartilage in order to facilitate the de-fatting and dehydration of the cartilage. Currently defatting and dehydration is accomplished in two stages: (1) the cartilage granules are immersed in several (3 to 5) times by volume of anhydrous acetone. The acetone removes the residual fat and partially dehydrates the cartilage; (2) the material from (1) is dried in a vacuum oven to reduce moisture content to less than 3%. The cartilage material is then pulverized in a cool ball mill with ceramic balls in the virtual absence of air or oxygen by flooding the free space in the mill with an inert gas. The grinding is continued until the desired particle size is obtained.

The cartilage powder so obtained can be utilized in powder form or extracted at a temperature between about 3° to 4° C. with distilled water or an aqueous salt solution which facilitates solubilization or peptizing of the cartilage material at low temperature. The solubilized cartilage obtained in this manner is not a true solution but rather is a colloidal dispersion containing between about 1 and 10% cartilage solids by weight.

It has now been unexpectedly discovered that the cartilage products described above can be prepared without the necessity of separate defatting and vacuum drying steps and that the enzyme-treated cartilage granules can be defatted and dehydrated by a single azeotropic extraction step.

Another aspect of the present invention is the unexpected discovery that the calcium content of shark cartilage granules can be removed easily by a simple mechanical agitation step conducted while the granules are only partially dried.

Accordingly, it is an aspect of the present invention to provide a method of processing animal cartilage without the necessity of separate defatting and vacuum drying steps.

Another aspect of the present invention is a method of processing animal cartilage to remove calcium without the necessity of liquification and separation steps.

The present invention involves a process for the preparation of cartilage products from raw animal or fish cartilage. As used herein, the term "raw cartilage" refers to cartilage from which the adhering tissues (primarily proteinaceous and fat) have been trimmed but not completely removed. Bovine cartilage (especially bovine tracheal cartilage) is a preferred raw material for use in the invention, however cartilage taken from other vertebrate animals including porcine and canine cartilage as well as cartilage from the partly calcified skeleton, including fetal skeleton, of very young or newly born animals will also provide suitable results.

Cartilage powder may also be obtained from cartilage sources such as pigs, lambs, goats, rodents, rib cage of crocodiles, birds, fish, etc. Reptile cartilage is particularly desirable in view of the ability of reptiles to regenerate their tissues and even their limbs. Cartilage from young animals or young or newly regenerated cartilage from older animals has also been found satisfactory for use in the present invention. Cartilage from mature animals in either the form which would in maturity retain the cartilaginous form or which would in maturity ossify to bone may also be employed. Skeletal cartilage from fish, particularly the shark, has also been found to provide an especially satisfactory raw material.

Cartilage from the skeletons of shark or other cartilaginous fish may be used to prepare cartilage products in the same manner as bovine cartilage. However, in the case of the shark, the spinal column is the most convenient tissue to harvest. Despite the fact that in most sharks the vertebrae are calcified to a considerable degree, they contain sufficient cartilage material to yield a useful product. While bovine trachea is a preferred source of raw cartilage, as it is the most readily accessible cartilaginous tissue in mammals, hyaline or costal cartilage from other parts of the animal's body may be utilized to produce satisfactory extracts.

Sharks have no bones but only cartilage in their skeletal structure. Depending on the age of the shark or its family within the species, the cartilage skeleton is covered with a calcified layer of from 5% to 80% of its weight. The gills have the least calcification while the spine has the most. Shark cartilage contains over 70% moisture and virtually no fat. Shark cartilage can be easily trimmed manually, however, an additional enzyme treatment is usually desirable in order to remove all adhering tissues.

The raw cartilage may be prepared by any satisfactory means but generally is obtained by removing substantially all of the skin, integument and organs of the animal or fish and separating the cartilage. The separated and trimmed cartilage, to which some proteinaceous tissue and fat will generally still be adhered may be subdivided into chunks or used in whole form as removed from the animal. The size of the raw cartilage pieces to be employed in the invention is not critical and is primarily dependent upon the dimensions of the reaction vessel in which the cartilage is to be processed.

To obtain a pure, dry product it is desirable to remove protein and fat from the trimmed cartilage. The protein is removed by proteolytic digestion. Digestion is accomplished using a solution containing a proteolytic enzyme which may be one or a combination of pepsin, papain, trypsin or other enzymes, in a dilute solution of hydrochloric or acetic acid. However the acid solutions are not used with papain or trypsin as these enzymes are denatured by acid. After the cartilage is separated from the enzymatic solution by washing with deionized or distilled water, the cartilage is granulated. The granules have an average diameter of from about 0.4 cm to 0.8 cm. An average diameter of about 0.6 cm is preferred. The granulated cartilage contains fat and has a high moisture content.

In one embodiment of the present invention, fat and moisture can be removed simultaneously by azeotropic extraction.

Azeotropic extraction utilizes the properties of certain solvents to form a mixture with another liquid, the composition of which does not change upon distillation. Thus, in the present invention, a solvent which is an effective defatting agent and forms an azeotrope with water, would be appropriate to use for azeotropic extraction.

Any solvent which meets the above criteria can be used to perform the azeotropic extraction. Examples of suitable defatting solvents for use in the present invention include benzene, toluene, hexane and heptane. A particularly useful solvent for use in the present invention is toluene. Toluene is a good defatting agent. Lipids are soluble in toluene and toluene forms an azeotrope with water. The toluene/water azeotrope has a composition of 79.8% toluene and 20.2% water and a boiling point of 85.0° C. If sufficient toluene is provided, all or substantially all of the moisture can be removed from the cartilage granules. The boiling toluene (at 85° C.) carries the water vapor with it. The water is separated from the toluene by a water trap and the toluene can thus be reused.

Benzene and water form an azeotrope having a composition of 91.1% benzene and 8.9% water, and a boiling point of 69.4° C. Hexane and water form an azeotrope having a composition of 94.4% hexane and 5.6% water and a boiling point of 61.6° C. Heptane and water form and azeotrope having a composition of 87.1% heptane and 12.9% water, and a boiling point of 79.2° C.

The azeotropic extraction process of the present invention is useful for extracting fats and water from cartilage granules, whether the granules have been enzyme-treated for the removal of protein or not.

The previous method of defatting and dehydrating the cartilage granules required separate defatting and drying steps as described above. For a typical batch of about 100 kg of granules, the defatting of granules by immersion in acetone is conducted for about 2 hours, followed by drying in a vacuum oven at 100° C. and at a vacuum of about 20 mm for about 10 hours to reduce moisture content to less than 3%. The present invention, on the other hand, combines the defatting and dehydrating steps in a single azeotropic extraction lasting about 5 hours for a batch of about 100 kg followed by a simple drying step of about 60 minutes duration at 90°–100° C. and at a low-vacuum of 20 mm to remove the azeotropic solvent. Thus, the method of the present invention results in a time savings of about fifty percent.

Another process of the present invention is the unexpected discovery that the calcium content of shark cartilage granules can be removed easily by a simple mechanical agitation step conducted while the granules are partially dried.

Certain types of cartilage have a calcified outside layer. The calcium compounds must be removed from the processed cartilage before the cartilage can be used therapeutically. Currently, calcium compounds are removed from the processed cartilage powder by placing the powder into solution and using separation techniques to remove the calcium compounds from the cartilage powder. The cartilage powder is then removed from solution and dried. This process requires a relatively large expenditure of energy to dry the powder after the calcium compounds have been extracted.

It has now been unexpectedly discovered that the calcium compounds associated with the processed cartilage powder can be separated from the powder without the necessity of employing liquid extraction techniques.

Cartilage granules treated with a defatting agent such as acetone, toluene, hexane or heptane, are partially dried in a convection vacuum oven for a short period of time. The semi-dry granules are tough and horny. However, the outside layer is calcified and friable. The semi-dry granules containing a calcified powder layer are subjected to mechanical agitation such as milling in a ball mill with ceramic balls totalling twice the weight of the cartilage granules for a short time (approximately 15 minutes) or until the calcified layer becomes powdery, while the underlying cartilage material remains partially unground. Consequently, the granules and powdered calcium compounds are separated by sieving. The cartilage granules are then processed further to prepare various cartilage products. This method of separating calcium compounds from cartilage granules is more economical in time and money than the prvious liquid extraction methods.

The present invention is further illustrated by the following working examples which are not intended to limit the invention in any respect.

EXAMPLE 1

500 grams of well trimmed calf cartilage was granulated in a meat grinder at 6° C. to form granules having an average diameter of 5 mm. The granulated cartilage was then loaded into a 3-liter round-bottom distilling flask. Toluene was then introduced to the vessel in an amount equal to twice the weight of the cartilage (i.e. 1000 ml of toluene). The vessel was equipped with a reflux condenser and a water trap. The vessel was then heated to the boiling temperature of the toluene, which was reduced to 85° C. due to the toluene/water azeotrope, and the boiling was continued until no more water was collected in the trap (3 hours). The toluene containing the lipids was then separated from the cartilage. The cartilage granules were then washed with some (300 ml) of fresh toluene at 17° C. and removed from the vessel. Residual toluene was stripped from the defatted and dehydrated granules by heating in a laboratory vacuum oven at about 80° C. until all the toluene odor has disappeared from the granules, approximately 3 hours.

Cartilage powder was obtained by grinding the dried and defatted cartilage granules in a ball mill to a desired particle size (preferably from 40 to 70 microns) under inert atmosphere. Nitrogen or $CO_2$ are suitable for use in providing an inert atmosphere, but other inert gases can also be used.

EXAMPLE 2

The powder of Example 1 was prepared, but the cartilage was enzyme-treated before granulation. The raw cartilage was treated with an aqueous solution of 2.5% acetic acid and 0.4% pepsin, NF grade, obtained from City Chemical Co., of New York, N.Y. The enzyme solution was introduced to the cartilage in an amount equal to 2.5 times the weight of the cartilage. The cartilage was exposed to the enzyme solution for 5 hours at 50° C. with mild agitation provided by a mixer obtained from Arde-Barinco of Mahwah, N.J. The enzyme-treated cartilage was then washed with deionized water at 18° C. until the pH of the effluent water was 5.5 or higher. The washed cartilage was centrifuged at 5000 rpm for 5 minutes to remove adhering water The cartilage was then granulated.

In a second embodiment of the present invention, cartilage may be granulated and then freeze-dried to remove moisture. Optionally, a defatting agent can be used before freeze-drying. The defatting agent may also contribute to dehydration. Anhydrous acetone, for example, acts to remove fat from the granulated cartilage and also partially dehydrates the cartilage. The following example illustrates the defatting/ freeze-drying process of the present invention for preparing cartilage powder.

EXAMPLE 3

1000 g of tiger shark cartilage from gills, hand trimmed, was treated with 2.5 times its weight of an aqueous solution of 2.5%, acetic acid and 0.4% pepsin NF grade (obtained from City Chemical Co.) at 50° C. for 5 hours with mild agitation provided by a mixer. The acid-pepsin treated cartilage was washed with deionized water at 18° C. until the pH of the effluent water was 5.5 or higher. The washed cartilage was placed in a basket centrifuge at 2000 rpm for 5 minutes to remove adhering water. The moist cartilage was then granulated in a meat grinder, coarse setting, to produce granules having an average diameter of 6 mm. The still moist cartilage granules were treated in a closed vessel with twice their weight of anhydrous acetone, for two hours with slow agitation (turbine rotor at 30 rpm). The acetone was then removed and the cartilage granules were dried for 20 minutes at 110° C. in a convection vacuum oven. The semi-dried granules were then transferred to a Virtis freeze-drier and dried until the moisture content of the granules dropped to 3.0% or lower, preferably to 0.5% or lower. The dried granules were then ground in a ball mill to fineness of 200-mesh sieve.

Alternatively, the enzyme-treated granulated cartilage can be freeze-dried without first performing a defatting step and by acetone extraction.

EXAMPLE 4

Tiger shark cartilage was treated with acid-pepsin as in Example 3. The cartilage was then granulated in a meat grinder at coarse setting. The still wet granules were then subjected to freeze drying in a Virtis freeze drier, without acetone extraction. The dried granules were then subjected to ball milling as in Example 3.

EXAMPLE 5

Tiger shark cartilage was processed as in Example 3 up to the point of freeze-drying. The semi-dried granules were tough and horny; however, the outside layer was calcified and friable. The semi-dried granules were placed in a laboratory ball mill with ceramic balls totaling twice the weight of the cartilage granules. The granules were milled for 15 minutes at which point the calcified layer became powdery, while the cartilage granules remained virtually unground. Consequently, the granules were readily separated by sieving. The yield was by weight of raw cartilage 80% cartilage granules containing 3.2% calcium phosphate. The semi-dried granules with reduced calcium content were then freeze-dried as in Example 3 and ground to a fineness of 100-mesh screen.

The final products from the Examples are suitable for use as therapeutic food supplements. The products in which the cartilage was enzyme-treated before processing it to the final product, are suitable for use in the treatments of the various indications described in my previous patents. Thus, the powder of the present invention can be used as a wound-healing medicant as described in my previous U.S. Pat. Re. 28,093, reissued July 30, 1974 from original U.S. Pat. No. 3,400,199, dated Sept. 3, 1968. The powder can also be used in dental applications including the treatment and prevention of dry sockets, gingival tissues and mandibular cystectomies, as described in my previous U.S. Pat. No. 3,772,432. The powder can also be used in the treatment of degenerative joint afflictions, such as osteoarthritis, as described in my earlier U.S. Pat. No. 3,966,908.

EXAMPLE 6

This example illustrates one use for the processed cartilage materials of the present invention. The preparation of a cartilage paste and its use for dental applications is illustrated. The figures given represent parts by weight.

|  | Stiff* | Medium* | Soft* |
|---|---|---|---|
| Calf cartilage powder of Example 2 | 70 | 50 | 30 |
| Isotonic saline solution (0.9% NaCl) | 30 | 50 | 70 |

*Refers to consistence characteristic of paste.

The paste in each case was prepared by weighing out the cartilage powder and placing it on a glass plate. The saline solution was added gradually and under constant mixing with a spatula. When a homogenous, well dispersed, lump-free paste was obtained it was ready for use.

The paste is used by introducing it directly in the dry socket, approximately 70% of its depth. The medium consistency paste was found to be the most easy to apply and it stayed in the sockets for almost a day. The stiff paste was somewhat less effective in relieving the pain from dry sockets, but it resisted the action of saliva more than the medium paste and stayed in the socket two days. The soft paste was flushed out of the dry sockets by saliva within about two hours.

The cartilage paste substantially stopped the pain from dry sockets in the dental patient within 15 to 30 minutes after application of the paste, the time being related to the consistency of the paste. The dry sockets so treated healed in a somewhat shorter time than is expected for normal extract sockets to heal. When the dry sockets were closed with a dental adhesive bandage or with a suture in the gum flaps, the cartilage paste of all three consistencies stayed in the socket throughout the healing period.

The cartilage paste has also been used to treat extraction sockets as a prophylactic measure. Such treatment prevents the occurrence of dry sockets in human beings.

As previously indicated, the cartilage product has use in other dental applications such as treatment of gingival tissues and mandibular cystectomies. Thus, the cartilage paste has been inserted in the filling of tooth cavities in combination with the amalgam filling. Without the cartilage paste such cavities when closed with the filling result in extremely painful pressure developing in the cavity thereby frequently necessitating the reopening of the cavity and treating the exposed nerve before the cavity can be refilled again. The inclusion of the cartilage paste in the cavity elimintes any pain that would otherwise result from exposed nerves in the cavity.

In the case of gingival tissues of various kinds, the cartilage paste is spread with a dental spatula in a thin layer on the under surface of the tissue prior to its fixation. Alternatively, the cartilage product can be applied by the atomization of cartilage powder or cartilage extract with an appropriate atomizer to form a thin "frost" on the surfaces which are to be opposed.

The cartilage compositions described herein may be used alone or in combination with wound healing accelerators such as polymeric N-acetyl-glycosamine (e.g. chitin) eggshell powder, etc. or antibiotics such as penicillin and other medicaments where it is desired to obtain some special additional effect.

What is claimed is:

1. A method of preparing finely divided cartilage powder from raw cartilage comprising:
   isolating raw cartilage from an animal body;
   granulating the raw cartilage into granules having an average size of from about 4 to 8 mm diameter;
   freeze drying the granules until the moisture content of the granules falls below 3.0%; and
   milling the granules to an average size of from about 40 to 70µ mm diameter.

2. The method of claim 1 further comprising treating the isolated cartilage with a proteolytic enzyme solution prior to said granulating step.

3. The method of claim 2 wherein said proteolytic enzyme solution is selected from the group consisting of pepsin, papain, trypsin, pepsin and hydrochloric acid, pepsin and acetic acid, and combintions thereof.

4. The method of claim 3 wherein said animal is a shark.

* * * * *